United States Patent [19]

Pfeiler et al.

[11] Patent Number: 4,709,385
[45] Date of Patent: Nov. 24, 1987

[54] X-RAY DIAGNOSTICS INSTALLATION FOR SUBSTRACTION ANGIOGRAPHY

[75] Inventors: Manfred Pfeiler; Johann Seissl, both of Erlangen, Fed. Rep. of Germany; Peter C. Block, Weston, Mass.

[73] Assignee: Siemens Aktiengesellschaft, Berlin and Munich, Fed. Rep. of Germany

[21] Appl. No.: 824,105

[22] Filed: Jan. 30, 1986

[30] Foreign Application Priority Data

Feb. 4, 1985 [DE] Fed. Rep. of Germany ....... 3503722

[51] Int. Cl.⁴ .......................... H05G 1/64; H04N 5/32
[52] U.S. Cl. ........................................ 378/99; 378/95; 358/111
[58] Field of Search ..................... 378/99, 95, 98, 114; 382/54, 6; 358/111

[56] References Cited

U.S. PATENT DOCUMENTS 4,204,225  5/1980  Mistretta .............................. 358/111
4,430,749  2/1984  Schardt ................................. 382/54
4,433,428  2/1984  Haendle et al. ........................ 378/99

Primary Examiner—Carolyn E. Fields
Assistant Examiner—Joseph A. Hynds
Attorney, Agent, or Firm—Hill, Van Santen, Steadman & Simpson

[57] ABSTRACT

An x-ray diagnostics installation for subtraction angiography has an image memory connected to an output of an x-ray image intensifier video chain which has a number of addresses for storing individual x-ray video signals obtained during a dynamic body cycle of a patient under observation. A differencing unit receives stored signals from the image memory as well as current video signals and substracts those signals to form a superimposed image. Entry and readout of signals to and from the image memory is under the command of a control unit which is connected to the patient through, for example, an EKG circuit for identifying selected occurrences in the body cycle under observation. Entry and readout of data from the image memory is thereby controlled in synchronization with the selected occurrences in the cycle.

12 Claims, 1 Drawing Figure

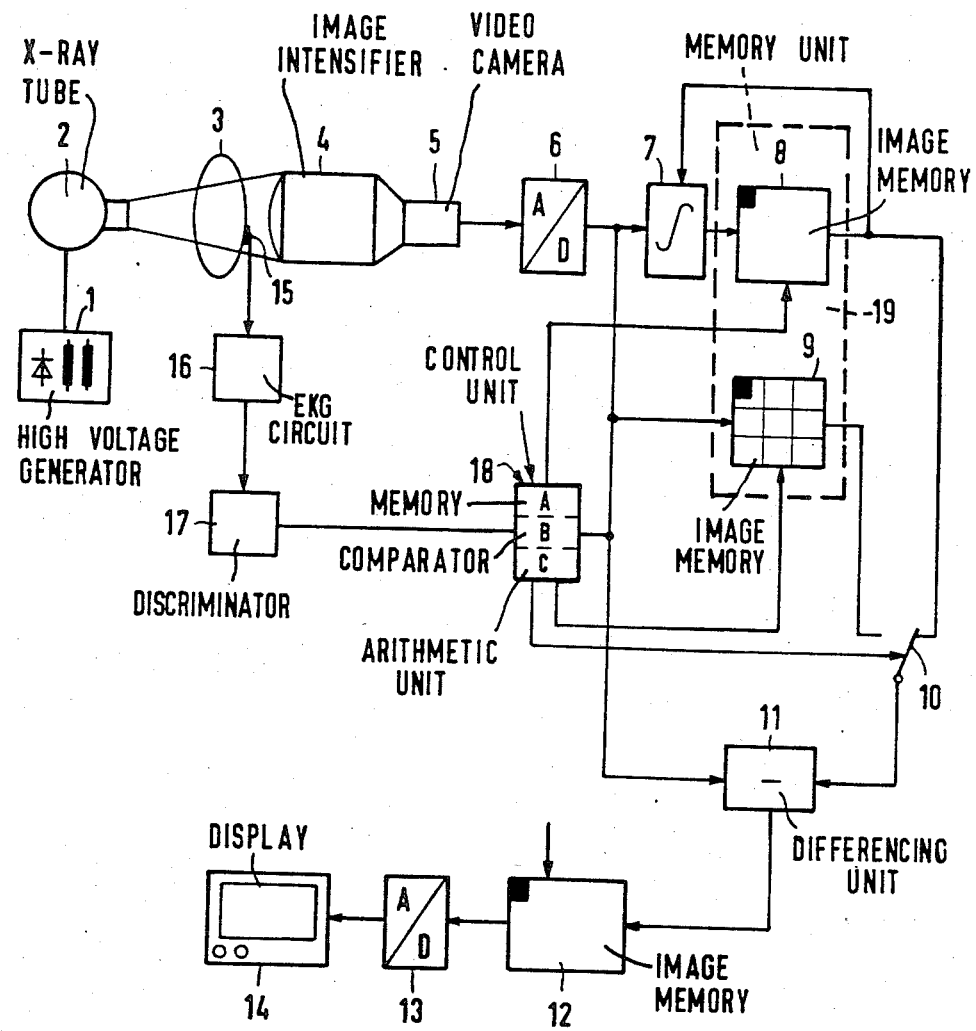

X-RAY DIAGNOSTICS INSTALLATION FOR SUBSTRACTION ANGIOGRAPHY

BACKGROUND OF THE INVENTION

1. Field of the Invention

The present invention relates to an x-ray diagnostics installation having an x-ray image intensifier video chain, an image memory and a differencing unit for subtracting stored video signals from current video signals, and in particular to such an installation having a control unit for controlling entry and readout of data from the image memory in accordance with selected occurrences in a dynamic body cycle of a patient under examination.

2. Description of the Prior Art

An x-ray diagnostics installation is described in German OS No. 31 24 583 correponding to U.S. Pat. No. 4,433,428 wherein a first image, which may be integrated, of a first heart phase is entered into a first image memory and a difference signal associated with a second heart phase is read into a second image memory. The second image memory is connected to a difference forming stage, which is also supplied with the current video signal as well as the stored video signal corresponding to the first heart phase. The current video signal and the first heart phase signal are subtracted, and the maximum expansion and maximum contraction of the heart, and thus the movement of the organ, can thereby be seen. A disadvantage of this installation, however, is that it cannot be employed in connection with another type of examination technique, known as the path-finder technique, described below.

In the so-called path-finder technique, a continuing fluoroscopic image showing a catheter is superimposed with the representation of the vessels generated from subtraction angiography. The examining physician or technician can thereby identify the course of the vessel paths when the catheter is introduced, without the use of a contrast agent, and make use of this information in correspondingly controlling the catheter. Transfer of the path-finder technique to cardiac angiography, however, is not possible in conventional installations because subtraction angiography generates a static vessel image which is superimposed on a radiograph which is dynamic, specifically with reference to the heart. Thus the contours of the moving heart coincide with the contour supplied by the subtraction image only at a single point in time.

SUMMARY OF THE INVENTION

It is an object of the present invention to provide an x-ray diagnostics installation which can be used in combination with the path-finder technique even in the case of dynamic events such as, for example, the human heart cycle.

The above object is inventively achieved in a method and apparatus wherein an image memory having a storage capacity for a plurality of individual images which arise during a heart cycle of the patient is inscribed and emptied of data under the command of a control device connected to a means for monitoring selected occurrences in the cycle under consideration. The control unit may, for example, be connected to an EKG circuit for identifying the various waves or blips in a heartbeat cycle. Entry of the individual images into the image memory thereby occurs at predetermined different heart phases of the heart cycle and readout of the individual images of the image memory is synchronized with the heart cycle signals from the EKG circuit such that individual images from the image memory are superimposed with current video signals within the heart cycle. The stored video signal of the vessel system associated with the same heart phase is thus superimposed on the current video signal in a radiography mode.

In a further embodiment of the invention, two image memories may be provided having outputs connected to a switching device which is in turn connected to one input of the differencing unit. The switching device connects one or the other of the two memory outputs through to the differencing unit. Switching of the switching devices under the command of the control unit which, as stated above, generates control signals in accordance with selected events identified in the dynamic cycle under examination. The additional memory is utilized to store an auxiliary mask which is generated during at least one cycle of the body cycle of interest, such as one heartbeat cycle, and which may be integrated over that cycle. After injection of a contrast agent into the patient, a number of successive images belonging to one heart cycle are entered in the second image memory dependent upon the maximum of the contrast agent curve in the region of interest. After entry of data in the additional memory is concluded, the switching element connects the second image memory to the differencing stage. A reliable entry of a complete heart cycle is achieved when the control device has means for identifying the heart cycle which is typical for the patient, and only effects entry into the second image memory when the current heart cycle corresponds to the typical heart cycle in terms of its duration. A more precise synchronization of the heart phases is achieved when the control device is an EKG unit, thereby obtaining a curve having identifiable features, i.e. the well-known waves or blips, which are used for synchronization. Optimum adaptation of the time duration of the individual heart phases is achieved when the control unit has means for varying the duration of the stored heart phase by interpolation of the individual images over time.

DESCRIPTION OF THE DRAWINGS

This single FIGURE is a schematic circuit diagram of an x-ray diagnostics installation constructed in accordance with the principles of the present invention.

DESCRIPTION OF THE PREFERRED EMBODIMENTS

An x-ray diagnostics installation is shown in the FIGURE having a high voltage generator 1 which feeds an x-ray tube 2, which generates an x-ray beam for irradiating a patient 3. An x-ray image intensifier 4 disposed in the beam path behind the patient 3 is connected to a video camera 5. The output signal of the video camera 5 is supplied to an analog-to-digital converter 6. The digital video signal is entered through an integration stage 7 into a first image memory 8. An output of the image memory 8 is fed back to a second input of the integration stage 7. The output signal of the analog-to-digital converter 6 is also connected to a second image memory 9, which has a storage capacity for several individual images. The outputs of the image memories 8 and 9 are connected through a switch 10 to one input of a differencing unit 11. The output of the converter 6 is supplied to the other input of the differencing unit 11.

The output signal of the differencing unit 11 is supplied to a third image memory 12, having an output connected to a digital-to-analog converter 13. The analog output of the converter 13 is displayed on a display device or monitor 14. Electrodes 15 such as, for example, EKG electrodes are connected to the patient 3 for supplying signals to a monitoring circuit 16 such as, for example, an EKG circuit of the type known to those skilled in the art. The output signal (EKG signal) of the circuit 16 is supplied to a discriminator 17 for the amplitude and phase of the EKG signal. The discriminator 17 is connected to a control unit 18 which controls entry of data into the two image memories 8 and 9. The EKG circuit 16, the discriminator 17 and the control unit 18 form a control chain which may be, for example, of the type described in aforementioned German OS No. 31 24 583.

Digital video signals are present at the output of the converter 6 after the fluoroscopy has been switched on. Integrated over at least one heart cycle, these video signals are entered in the first image memory 8 as an auxiliary mask. The switch 10 connects the output of the first image memory to the differencing unit 11. Subsequent thereto, the patient 3 is injected with a contrast agent which can be seen in the region of interest in the subtraction image on the display 14 with a slight time shift. Entry of data into the second image memory 9 is automatically or manually initiated at a time when the contrast agent concentration of the stored images reaches a maximum. After the appearance of a recognizable feature of the EKG signal such as, for example, the R-wave, the exposures for different heart phases of a heart cycle are stored in the image memory 9 as a mask cycle. After conclusion of the data entry, the switch 10 is actuated by the control unit 18 so that the output of the second image memory 9 is connected to the differencing unit 11. The individual images stored in the second image memory 9 are read out synchronous in heart phase to the current video signal. As a result, the vessel system can be seen on the display 14 as a bright image superimposed on the remaining picture contents. A catheter can then be introduced into the vessels which have been made visible in this manner and can be correctly guided. As a consequence of the readout of the image memory 9 in synchronized heart phase to the current video signal, corresponding individual images are subtracted, thereby guaranteeing in all instances that the vessels obtained from the stored image correspond to real curves and contours.

If the complete heart cycle is to be entered into the second image memory 9, so that a very precise superposition can be achieved, the memory 9 must have a storage capacity of about 50 through 60 fields. The storage capacity may be reduced, however, if only every second or third field is stored, which results in images of the heart cycle which are sufficiently precise for many applications.

Because the heart cycles are not always identical, for example an extra systole may appear, the control device 18 has means in the form of an arithmetic unit 18C for determining the length of an average typical heart cycle before entry of the mask cycle into the second image memory 9. This average duration is stored in a memory 18A in the control unit 18. When entry of data into the second image memory 9 begins, the duration of the current heart cycle is compared to the stored typical duration in a comparator 18B in the control unit 18. Given equality of the durations, the data entry is terminated. If, however, a deviation in the duration of the current heart cycle from the stored typical heart cycle is observed, the old images are erased in the image memory 9 and the next heart cycle is entered.

For reproducing images, the beginning of the readout of data from the second image memory 9 is always synchronized with a recognizable event in the cycle of interest such as, for example, the R-wave of the EKG signal. Differences in the period duration are compensated by the omission of the last images or by repeated readout thereof. If, for example, the heart cycle is already subdivided into a plurality of segments during data entry such as, for example, it is synchronized to a plurality of identifiable features of the EKG signal, this can also occur during image reproduction. An equalization of the duration is thereby already achieved by equalizing the segments, so that the dynamic representation of the vessels better corresponds to the actual contours. The duration of the heart cycle may, however, be adapted to the current heart cycle by interpolation of the stored individual images on the time axis.

As shown in the drawing, the image memories 8 and 9 may be separate units or may be combined in a single memory unit 19, in which case the image memory 8 may simply be characterized as an address location of the second image memory 9. When entry of the heart cycle data is initiated, the auxiliary mask is no longer required, so that this memory location can be overwritten. As a result, the switch 10 can also be eliminated, so that the image memory 9 is always connected to the differencing unit 11. The third image memory 12, which is preferably a mask storage, records individual images, and is not absolutely required for all x-ray diagnostics installations.

Although modifications and changes may be suggested by those skilled in the art it is the intention of the inventors to embody within the patent warranted hereon all changes and modifications as reasonably and properly come within the scope of their contribution to the art.

We claim as our invention:

1. An x-ray diagnostics installation for monitoring a dynamic body cycle of a patient comprising:
    means for generating an x-ray beam directed at said patient;
    an x-ray image intensifier video chain for generating a video signal from x-rays passing through said patient;
    an image memory connected to an output of said image intensifier video chain having a plurality of addresses for storing a plurality of individual x-ray video signals obtained during said body cycle;
    a differencing unit connected to an output of said image memory and to said output of said image intensifier video chain for subtracting a stored video signal from a current video signal;
    pick-up means connected to said patient for identifying a plurality of selected occurrences in said cycle; and
    control means for said image memory connected to said pick-up means for enabling entry of said video signals into said image memory following one of said selected occurrences and enabling readout of said image memory to said differencing unit synchronous with said occurrences for superimposing said current video signal on said plurality of video signals obtained during said cycle.

2. An x-ray diagnostics installation as claimed in claim 1 further comprising:
memory means connected to said output of said image intensifier video chain and controlled by said control means for storing an auxiliary mask integrated over at least one body cycle; and
means for selectively connecting said memory means to said differencing unit.

3. An x-ray diagnostics installation as claimed in claim 2 wherein said memory means is at least one memory location in said image memory.

4. An x-ray diagnostics installation as claimed in claim 2 wherein said memory means is an additional image memory, and wherein said means for selectively connecting is a switch controlled by said control means having inputs connected to respective outputs of said image memory and said additional image memory, and an output connected to said differencing unit.

5. An x-ray diagnostics installation as claimed in claim 1 wherein said body cycle is a heart cycle, and wherein said pick-up means is an EKG unit.

6. An x-ray diagnostics installation as claimed in claim 5 wherein said one of said selected occurrences in said cycle is the R-wave of said heart cycle.

7. An x-ray diagnostics installation as claimed in claim 6 wherein said readout of said image memory is synchronized with segments of said heart cycle between identifiable waves of an EKG signal generated by said EKG unit.

8. An x-ray diagnostics installation as claimed in claim 1 wherein said control means includes:
arithmetic means for determining a typical duration of said body cycle;
memory means for storing said typical duration; and
means for comparing said stored typical duration with a current body cycle duration and for generating a control signal for controlling entry of data into said image memory based on the result of the comparison.

9. An x-ray diagnostics installation as claimed in claim 1 wherein said control means includes means for varying the duration of a stored body cycle in said image memory by time-interpolation of individual images stored in said image memory.

10. A method for monitoring a dynamic body cycle of a patient comprising the steps of:
irradiating said patient with an x-ray beam;
generating a video signal from the interaction of said x-ray beam with said patient;
monitoring a plurality of occurrences in said body cycle and generating signals corresponding to said occurrences;
controlling entry of a plurality of video signals comprising a plurality of video images into an image memory by at least one of said signals corresponding to said occurrences;
controlling readout of said video images from said image memory by said signals corresponding to said occurrences; and
forming a difference between an output of said image memory and a current video signal for superimposing said current video signal on said plurality of video signals obtained during each body cycle.

11. A method as claimed in claim 10 comprising the additional steps of:
injecting a contrast agent into said patient; and
beginning entry of said video signals into said image memory when the concentration of said contrast agent in said patient is a maximum.

12. A method as claimed in claim 10 comprising the additional steps of:
determining the duration of a typical body cycle;
storing said typical cycle duration;
comparing said stored typical duration to a current cycle duration so as to obtain a comparison result; and
controlling entry of data into said image memory based on said comparison result.

* * * * *